(12) United States Patent
Perugupalli et al.

(10) Patent No.: US 9,636,064 B2
(45) Date of Patent: May 2, 2017

(54) SYSTEM AND METHOD FOR MONITORING A SUBJECT'S EYE (71) Applicants: IMEC India Private Limited, Bangalore (IN); IMEC VZW, Leuven (BE)

(72) Inventors: Prasanth Perugupalli, Hyderabad (IN); Sumit Kumar Nath, Bangalore (IN)

(73) Assignees: IMEC India Private Limited, Bangalore (IN); IMEC VZW, Leuven (BE)

( * ) Notice: Subject to any disclaimer, the term of this patent is extended or adjusted under 35 U.S.C. 154(b) by 0 days.

(21) Appl. No.: 14/859,263

(22) Filed: Sep. 19, 2015

(65) Prior Publication Data

US 2016/0106355 A1    Apr. 21, 2016

(30) Foreign Application Priority Data

Sep. 19, 2014  (IN) .......................... 4572/CHE/2014

(51) Int. Cl.
*A61B 3/14* (2006.01)
*A61B 3/00* (2006.01)
*A61B 5/18* (2006.01)
*A61B 5/00* (2006.01)
*A61B 5/11* (2006.01)
*B60K 28/06* (2006.01)
*A61B 3/113* (2006.01)
*G06K 9/00* (2006.01)
*G06K 9/46* (2006.01)
*B60W 40/08* (2012.01)

(52) U.S. Cl.
CPC ................ *A61B 5/18* (2013.01); *A61B 3/113* (2013.01); *A61B 3/14* (2013.01); *A61B 5/0075* (2013.01); *A61B 5/1103* (2013.01); *B60K 28/06* (2013.01); *B60W 40/08* (2013.01); *G06K 9/0061* (2013.01); *G06K 9/4661* (2013.01); *B60W 2040/0827* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 2007/0296809 | A1* | 12/2007 | Newbery | ........... H04N 13/0239 348/42 |
| 2012/0212636 | A1* | 8/2012 | Haikin | .................. H04N 5/232 348/222.1 |
| 2012/0213407 | A1* | 8/2012 | Haikin | .............. G06F 17/30247 382/103 |
| 2012/0249821 | A1* | 10/2012 | Imai | ................... H04N 5/23229 348/222.1 |

\* cited by examiner

*Primary Examiner* — Mohammed Hasan
(74) *Attorney, Agent, or Firm* — McDonnell Boehnen Hulbert & Berghoff LLP (57) ABSTRACT

A system and a method for monitoring subject's eyes are disclosed. In one embodiment, spectral profiles of a frame substantially around a subject's eye are received from an image capturing device. Further, a state of the subject's eye in the frame is detected using the spectral profiles received from the image capturing device.

20 Claims, 7 Drawing Sheets

SYSTEM AND METHOD FOR MONITORING A SUBJECT'S EYE

CROSS-REFERENCE TO RELATED APPLICATION

The present application is a non-provisional patent application claiming priority to Indian Patent Application No. 4572/CHE/2014 filed on Sep. 19, 2014, the contents of which are hereby incorporated by reference.

TECHNICAL FIELD

Embodiments of the present subject matter relate to monitoring subject's eyes. More particularly, embodiments of the present subject matter relate to monitoring the subject's eyes to detect subject's wakefulness or drowsiness.

BACKGROUND

Typically, a subject is monitored to detect subject's wakefulness or drowsiness for taking an action when the subject is falling asleep. For example, the subject may be a vehicle driver, a person watching television and so on. In case of the vehicle driver, driver's drowsiness or wakefulness is detected and alerts may be sent to the driver to increase the attention while driving. An existing driver vigilance monitoring method is to monitor driver's facial expressions captured using an RGB camera and determine a drowsiness state of the driver based on movements of various muscles in the driver's face. The RGB camera requires illumination for capturing the driver's facial expressions. Therefore, a flash source may be used by the RGB camera for capturing the driver's facial expressions which can distract the driver during night time. Further, this method may recreate the face of the driver to localize the eyes for detecting driver's wakefulness or drowsiness. Another existing driver vigilance monitoring method is to monitor deviation from lane markings on the road and alert the driver when such deviations rise to dangerous levels. However, this method may provide false alerts to the driver when the vehicle deviation from the lane markings is caused due to distorted movement of vehicle wheels.

SUMMARY

A system and a method for monitoring a subject's eye are disclosed. According to one aspect of the present subject matter, spectral profiles of a frame substantially around a subject's eye are received from an image capturing device. Further, a state of the subject's eye in the frame is detected using the received spectral profiles.

According to another aspect of the present subject matter, a camera system includes an image capturing device and an eye monitoring system communicatively connected to the image capturing device. In one embodiment, the image capturing device captures spectral profiles from a frame substantially around a subject's eye. Further, the eye monitoring system receives the spectral profiles from the image capturing device and detects a state of the subject's eye in the frame using the received spectral profiles.

According to an example embodiment, there is provided a method for monitoring a subject's eye, including receiving spectral profiles of a frame substantially around a subject's eye from an image capturing device, and detecting a state of the subject's eye in the frame using the received spectral profiles.

According to another example embodiment, detecting the state of the subject's eye in the frame using the received spectral profiles may include determining spectral profiles of an eye and skin including an eyelid in the received spectral profiles, determining a number of the spectral profiles of the eye and a number of the spectral profiles of the skin including the eyelid, determining a ratio of the number of the spectral profiles of the eye and the number of the spectral profiles of the skin including the eyelid, and detecting the state of the subject's eye in the frame based on the determined ratio.

According to another example embodiment, determining the spectral profiles of the eye in the received spectral profiles may include determining spectral profiles of at least one or a combination of pupil, iris, and sclera in the received spectral profiles.

According to another example embodiment, determining the spectral profiles of the eye and the skin including the eyelid in the received spectral profiles may include obtaining spectral profiles of a reference frame substantially around the subject's eye, comparing the received spectral profiles of the frame with the spectral profiles of the reference frame, and determining the spectral profiles of the eye and the skin including the eyelid in the received spectral profiles based on the comparison.

According to another example embodiment, detecting the state of the subject's eye in the frame based on the determined ratio may include determining whether the ratio is greater than a predetermined threshold, if so, detecting the state of the subject's eye in the frame as an open state, and if not, detecting the state of the subject's eye in the frame as a closed state or a partially open state.

According to another example embodiment, the method may further include repeating the steps of receiving spectral profiles of a frame substantially around a subject's eye from an image capturing device, and detecting a state of the subject's eye in the frame using the received spectral profiles for a number of subsequent frames substantially around the subject's eye to detect a state of the subject's eye in the number of subsequent frames.

According to another example embodiment, the method may further include generating an alert based on the state of the subject's eye in the frame and the number of subsequent frames.

According to another example embodiment, the method may further include determining whether the ratio of the number of the spectral profiles of the eye and the number of the spectral profiles of the skin including the eyelid is changing over the frame and the number of subsequent frames, and detecting a drowsiness state of the subject when the ratio is changing over the frame and the number of subsequent frames.

According to another example embodiment, the method may further include generating an alert upon detecting the drowsiness state of the subject.

According to another example embodiment, detecting the drowsiness state of the subject when the ratio is changing over the frame and the number of subsequent frames may include detecting the drowsiness state of the subject when the ratio is decreasing over the frame and the number of subsequent frames.

According to another example embodiment, detecting the drowsiness state of the subject when the ratio is changing over the frame and the number of subsequent frames may include detecting gradual drowsiness of the subject when the ratio changes gradually over the frame and the number of subsequent frames, and detecting persistent drowsiness of the subject when the ratio changes significantly over the frame and the number of subsequent frames.

According to another aspect of the present subject matter, there is provided a computer program and a non-transitory computer-readable storage medium comprising instructions executable by a computing device which implement the method for monitoring a subject's eye according to example embodiments herein described.

The system and method described herein may be implemented in any device, system, hardware, and/or software configured to achieve various aspects. Other features will be apparent from the accompanying drawings and from the detailed description that follow.

BRIEF DESCRIPTION OF THE DRAWINGS

Various embodiments are described herein with reference to the drawings described below.

The drawings described herein are for illustration purposes only and are not intended to limit the scope of the present disclosure in any way.

DETAILED DESCRIPTION

A system and method for monitoring subject's eyes are disclosed. In the following detailed description of the embodiments of the present subject matter, references are made to the accompanying drawings that form a part hereof, and in which are shown by way of illustration specific embodiments in which the present subject matter may be practiced. These embodiments are described in sufficient detail to enable those skilled in the art to practice the present subject matter, and it is to be understood that other embodiments may be utilized and that changes may be made without departing from the scope of the present subject matter. The following detailed description is, therefore, not to be taken in a limiting sense, and the scope of the present subject matter is defined by the appended claims.

Embodiments described herein provide methods, techniques, and systems for monitoring subject's eyes. The example technique receives spectral profiles of a frame substantially around a subject's eye from an image capturing device. Further, the example technique determines spectral profiles for an eye and skin including an eyelid in the spectral profiles. In one example, the spectral profiles of the eye include spectral profiles of pupil, iris and/or sclera. Furthermore, the example technique determines a rate at which the subject's eye is open or closed using the spectral profiles of the eye and the spectral profiles of the skin including the eyelid.

Figure 1:
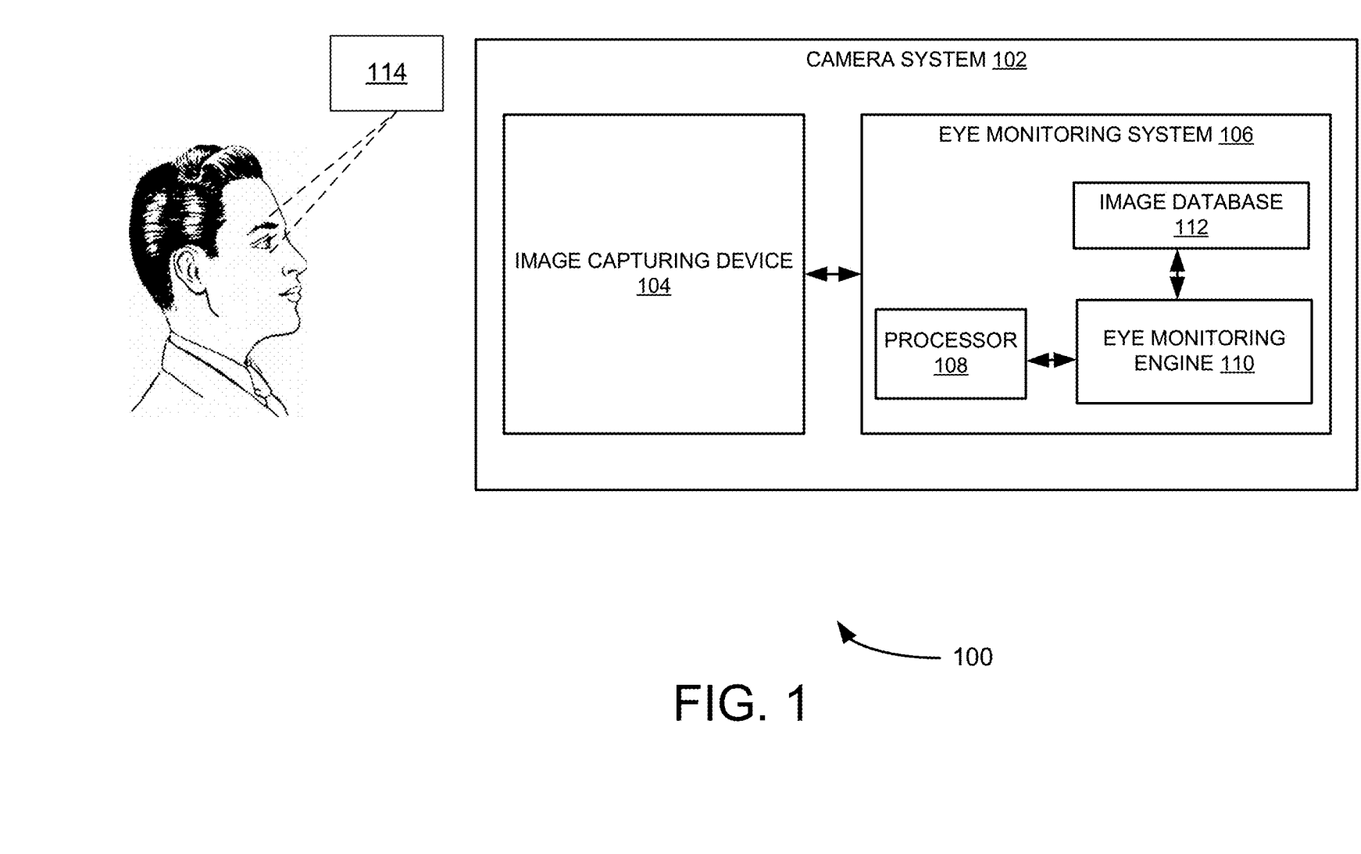
FIG. 1 illustrates a block diagram including an example camera system for monitoring subject's eyes, according to one embodiment.

FIG. 1 illustrates a block diagram 100 including an example camera system 102 for monitoring subject's eyes, according to one embodiment. For example, the subject can be a vehicle driver, a user operating an electronic device and so on. As shown in FIG. 1, the camera system 102 includes an image capturing device 104 (e.g., any camera that can capture hyper-spectral profiles of each pixel in a frame) and an eye monitoring system 106 communicatively connected to the image capturing device 104. Further, the eye monitoring system 106 includes a processor 108, an eye monitoring engine 110 coupled to the processor 108 and an image database 112 coupled to the eye monitoring engine 110. The eye monitoring engine 110 can represent any combination of circuitry and executable instructions to monitor the subject's eyes.

In operation, the image capturing device 104 captures spectral profiles from a reference frame substantially around a subject's eye. For example, the reference frame refers to a frame that is used as a reference for predicting future frames. For example, when the subject is a vehicle driver, spectral profiles are captured from a reference frame substantially around a driver's eye before start of a journey. Spectral profiles are plots of reflectance values for different points or regions over a range of wavelengths. Further, the image capturing device 104 stores the spectral profiles of the reference frame in the image database 112.

In the present example, the image capturing device 104 captures spectral profiles from a frame substantially around the subject's eye, in real-time. In one example, the image capturing device 104 is placed at a gross position with respect to height of the subject such that the image capturing device 104 can capture spectral profiles from the frame substantially around the subject's eye. In this example, the image capturing device 104 captures the spectral profiles from the frame using a light source 114 (e.g., a near infra-red (NIR) light source and the like) that does not distract the subject. For example, the light source 114 can be positioned in such a way to illuminate the subject's eyes.

Figure 2:
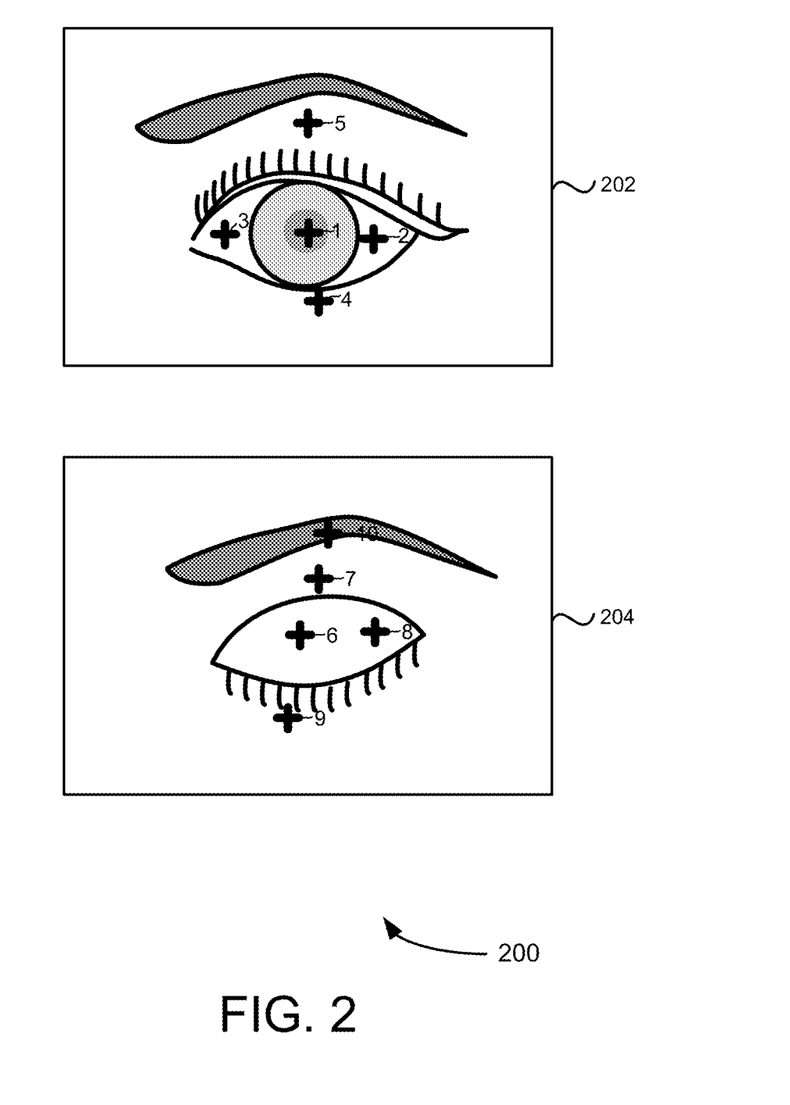
FIG. 2 is a schematic view illustrating frames around a subject's eye when it is open and closed, according to one embodiment.
Figure 3A:
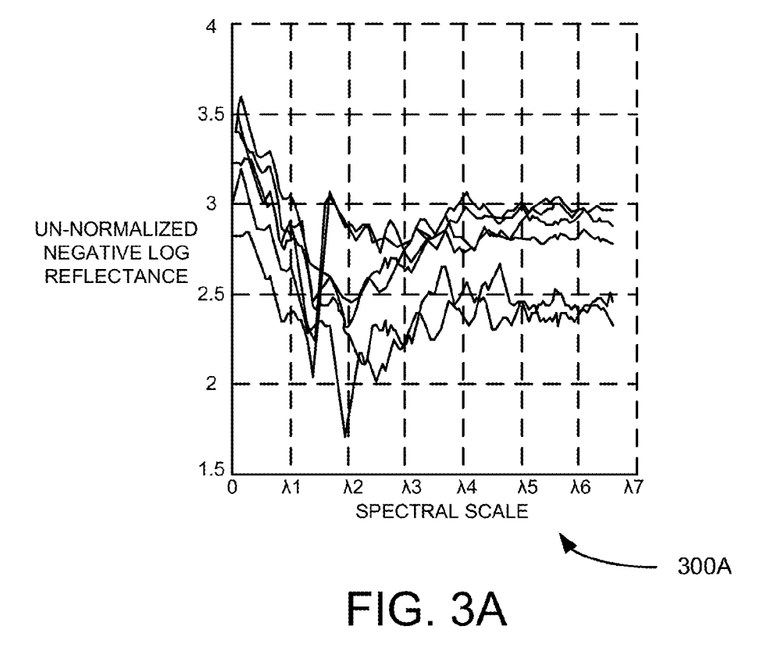
FIGS. 3A-3C are graphs illustrating example spectral profiles for points within and outside the subject's eye when the subject's eye is open and on skin including eyelids when the subject's eye is closed, such as those shown in FIG. 2, according to one embodiment.
Figure 3B:
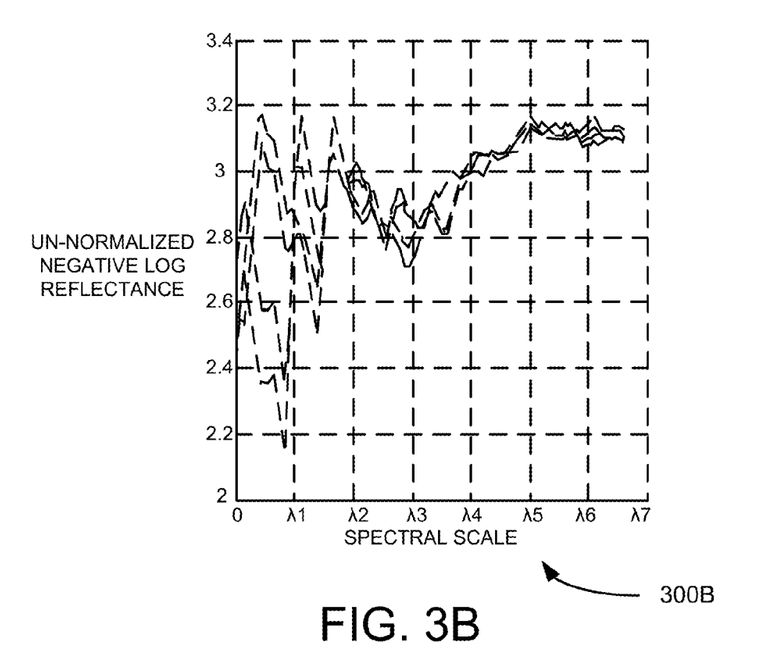
Figure 3C:
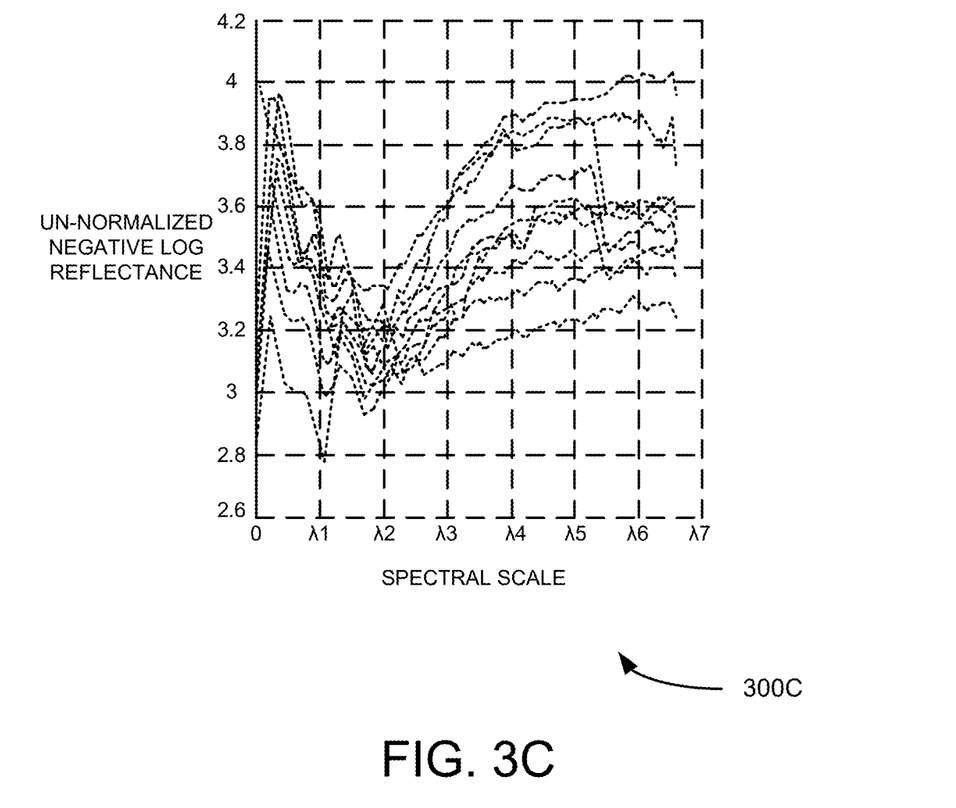

Also in operation, the eye monitoring engine 110 receives the spectral profiles of the frame from the image capturing device 104. In some embodiments, the eye monitoring engine 110 then compares the frame with the reference frame to determine whether there is a deviation in the subject's position (i.e., the subject is not in a field of view). If there is a deviation in the subject's position, then the eye monitoring engine 110 generates an alarm to the subject. If there is no deviation in the subject's position, then the eye monitoring engine 110 determines spectral profiles of an eye and skin including an eyelid in the received spectral profiles. In one example, the spectral profiles of the eye include spectral profiles of pupil, iris, and/or sclera. In one embodiment, the eye monitoring engine 110 determines the spectral profiles of the eye and the skin including the eyelid in the frame by comparing the received spectral profiles of the frame with the spectral profiles of the reference frame stored in the image database 112. The spectral profiles of eyes and skin including eyelids are different as the eyes have more absorbance capacity due to fluid content present in the eyes and the skin has more reflectance capacity. Example frames, including various points, around a subject's eye when it is open and closed are shown in FIG. 2. Example spectral profiles for points, shown in FIG. 2, within and outside the subject's eye when the subject's eye is open are shown in FIGS. 3A and 3B. Example spectral profiles for points, shown in FIG. 2, on skin including an eyelid when the subject's eye is closed are shown in FIG. 3C.

Further in this embodiment, the eye monitoring engine 110 determines a number of the spectral profiles of the eye and a number of the spectral profiles of the skin including the eyelid in the frame. Furthermore, the eye monitoring engine 110 determines a ratio of the number of the spectral profiles of the eye and the number of the spectral profiles of the skin including the eyelid in the frame. The eye monitoring engine 110 then detects a state of the subject's eye (i.e., one of an open state, a partially open state, and a closed state) in the frame based on the determined ratio. In one example, the eye monitoring engine 110 detects the state of the subject's eye as the open state when the determined ratio is greater than a predetermined threshold (which is a ratio determined empirically and stored in the image database 112). In another example, the eye monitoring engine 110 detects the state of the subject's eye as the closed state or the partially open state when the determined ratio is less than the predetermined threshold.

For example, a spectral profile of an eye is indicated as "A" and a spectral profile of skin (eyelid, forehead or any skin) is indicated as "B". Further, a predetermined threshold of a ratio of a frequency of the spectral profiles of the eye and the skin is 3. In one example, if the spectral profiles captured from a frame are "AAABAAAAA", then it is found that the ratio of the frequency of the spectral profiles of the eye and the skin is 8 (or 8:1) which is greater than the predetermined threshold and thus, indicating that a state of the subject's eye is an open state. In another example, if the spectral profiles captured from a frame are "ABAAB-BABA", then it is found that the ratio of the frequency of the spectral profiles of the eye and the skin is 1.25 (or 5:4) which is less than the predetermined threshold and thus, indicating that the state of the subject's eye is a partially open state. In yet another example, if the spectral profiles captured from a frame are "ABBBBBBBB", then it is found that the ratio of the frequency of the spectral profiles of the eye and the skin is 0.125 (or 1:8) which is less than the predetermined threshold and thus, indicating that the state of the subject's eye is a closed state.

In some embodiments, the eye monitoring engine 110 receives spectral profiles of a number of subsequent frames substantially around the subject's eye from the image capturing device 104 and detects a state of the subject's eye in the subsequent frames based on the received spectral profiles. The eye monitoring engine 110 then generates an alert based on the state of the subject's eye in the frame and the subsequent frames.

In one example, when the subject is a vehicle driver, the eye monitoring engine 110 detects a drowsiness state of the driver based on the state of the driver's eye in the frame and the subsequent frames and generates a level of alert (e.g., an alarm, voice communication asking the driver to take a break, and so on) upon detecting the drowsiness state of the driver. For example, the drowsiness state includes gradual drowsiness or persistent drowsiness. In one embodiment, the gradual drowsiness of the driver refers to a state when a ratio of a number of spectral profiles of the eye and a number of spectral profiles of the skin including the eyelid in each of the frame and the subsequent frames changes gradually over the frames. In another embodiment, the persistent drowsiness of the driver refers to a state when the ratio changes significantly over the frames, e.g., the driver's eye is closed in the frame and the subsequent frames. This is explained in more detailed with reference to FIG. 5.

In another example, when the subject is a person watching a television, the eye monitoring engine 110 generates an alert or an instruction to place the television into a power saving mode (e.g., a standby mode or a powered-off mode) when the ratio changes over the frames (e.g., the person's eyes are closed in the frame and the subsequent frames or the person is falling asleep).

For example, an open state of a subject's eye is indicated as "O" and a closed state of the subject's eye is indicated as "C". In one example, if states of the subject's eye in a sequence of frames are "OOOCOOO", then it is found that a ratio of a frequency of spectral profiles of an eye and skin is not changed over the frames and thus, indicating that the subject is awake or blinking normally. In another example, if states of the subject's eye in a sequence of frames are "OCOOCCOCO", then it is found that the ratio of the frequency of the spectral profiles of the eye and the skin is changed gradually over the frames and thus, indicating that the subject is falling asleep. In yet another example, if states of the subject's eye detected in a sequence of frames are "OCCCCCCCC", then it is found that the ratio of the frequency of the spectral profiles of the eye and the skin is changed significantly over the frames and thus, indicating that the subject's eye is closed in the frames or the subject is not looking at the road or the subject is not in the field of view.

Referring now to FIG. 2, which is a schematic view 200 illustrating frames 202 and 204 around a subject's eye when it is open and closed, respectively, according to one embodiment. Also, the frame 202 includes various points or regions, selected randomly, (indicated with bold plus marks 1-5) within and outside the subject's eye, when the subject's eye is open, for which the spectral profiles need to be determined. Further, the frame 204 includes various points or regions, selected randomly, (indicated with bold plus marks 6-10) on the skin including eyelids, when the subject's eye is closed, for which the spectral profiles need to be determined. Referring now to FIGS. 3A-3C, which are graphs 300A-300C illustrating example spectral profiles for the various points or regions within and outside the subject's eye (points 1-5) when it is open and on the skin including eyelids (points 6-10) when the subject's eye is closed, such as those shown in the frames 202 and 204, respectively. As shown in the graphs 300A-300C, the x-axis indicates a spectral scale and the y-axis indicates un-normalized negative log reflectance values. Particularly, the graph 300A illustrates the spectral profiles for the various points or regions (points 1-3) within the subject's eye when the subject's eye is open. Further, the graph 300B illustrates the spectral profiles for the various points or regions (points 4 and 5) across subjects (Caucasian/Asia, male/female and the like). Furthermore, the graph 300C illustrates the spectral profiles for the various points or regions (points 6-10) across subjects. As shown in FIGS. 3A-3C, the spectral profiles become flat when the points or regions lie within the subject's eye, while they show a (nearly) monotonic increase when the points or regions are on the eyelid.

Figure 4:
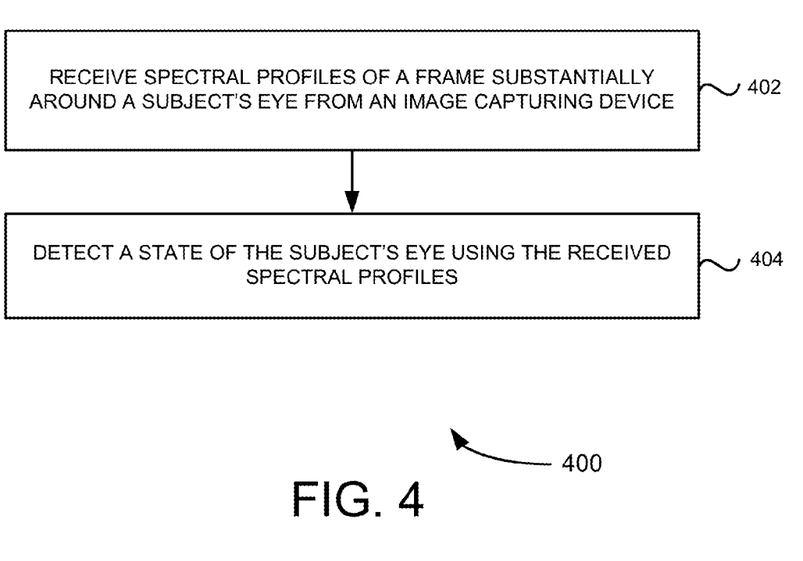
FIG. 4 illustrates a flow chart of an example method for monitoring subject's eyes, according to one embodiment.

Referring now to FIG. 4, which illustrates a flow chart 400 of an example method for monitoring subject's eyes, according to one embodiment. For example, the subject can be a vehicle driver, a user operating an electronic device and the like. At block 402, spectral profiles of a frame substantially around a subject's eye are received from an image capturing device. In one example implementation, the spectral profiles from the frame are captured using the image capturing device (e.g., a camera that can capture hyper-spectral profiles of each pixel in a frame). In this example implementation, a light source (e.g., a NIR light source) which does not distract the subject is used by the image capturing device. At block 404, a state of the subject's eye is detected using the received spectral profiles. For example, the state of the subject's eye includes an open state, a partially open state or a closed state. In one embodiment, spectral profiles of an eye and skin including an eyelid are determined in the received spectral profiles. In an example embodiment, the received spectral profiles of the frame are compared with spectral profiles that are obtained from a reference frame substantially around the subject's eye and the spectral profiles of the eye and the skin including the eyelid are then determined in the received spectral profiles based on the comparison. For example, the reference frame refers to a frame that is used as a reference for predicting future frames. For example, when the subject includes a vehicle driver, spectral profiles are captured from various points in a reference frame substantially around a driver's eye before start of a journey. Example frames including various points around a subject's eye when open and closed are shown in FIG. 2. Example spectral profiles for points, shown in FIG. 2, within and outside the subject's eye when it is open are shown in FIGS. 3A and 3B. Example spectral profiles for points, shown in FIG. 2, on skin including an eyelid when the subject's eye is closed are shown in FIG. 3C.

Further in this embodiment, a number of the spectral profiles of the eye and a number of the spectral profiles of the skin including the eyelid are determined. Furthermore, a ratio of the number of the spectral profiles of the eye and the number of the spectral profiles of the skin including the eyelid is determined. The state of the subject's eye in the frame is then detected based on the determined ratio. In one example, a check is made to determine whether the ratio is greater than a predetermined threshold. The state of the subject's eye in the frame is then detected as an open state when the determined ratio is greater than the predetermined threshold. The state of the subject's eye in the frame is then detected as a closed state or a partially open state when the determined ratio is less than the predetermined threshold.

In some embodiments, the process steps of 402 and 404 are repeated to detect the state of the subject's eye in a number of subsequent frames substantially around the subject's eye. Further, an alert is generated based on the state of the subject's eye in the frame and subsequent frames. In one example, a check is made to determine whether the ratio of the number of the spectral profiles of the eye and the number of the spectral profiles of the skin including the eyelid is changing over the frame and the number of subsequent frames. A drowsiness state of the subject is then detected when the ratio is changing over the frame and the number of subsequent frames. For example, the drowsiness state includes gradual drowsiness or persistent drowsiness. Further, an alert is generated upon detecting the drowsiness state of the subject. This is explained in more detail with reference to FIG. 5.

Figure 5:
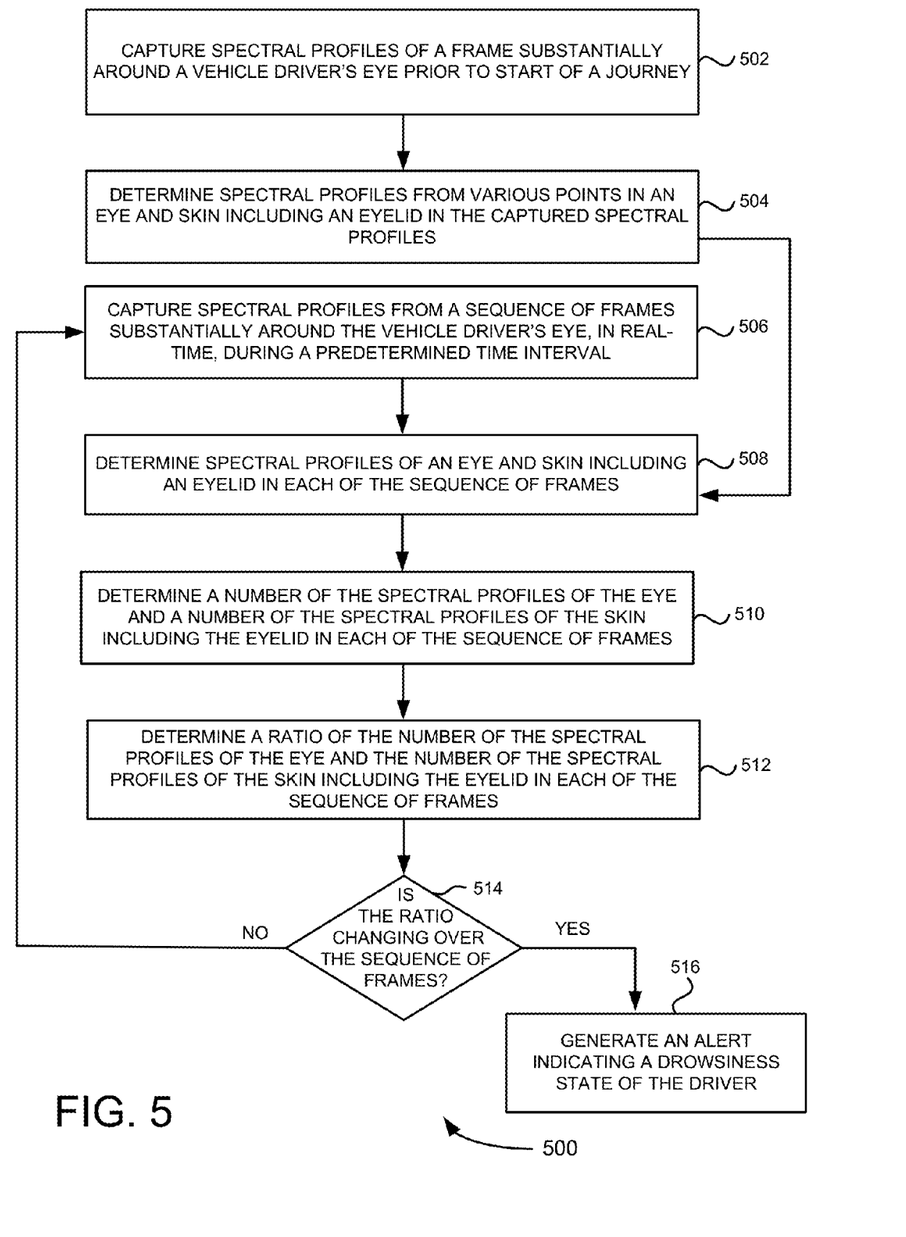
FIG. 5 illustrates a flow chart of a detailed process for monitoring vehicle driver's eyes, according to one embodiment.

Referring now to FIG. 5, which illustrates a flow chart 500 of a detailed process for monitoring vehicle driver's eyes, according to one embodiment. At block 502, spectral profiles of a frame substantially around the vehicle driver's eye prior to start of a journey are captured by an image capturing device. The spectral profiles of the frame are captured with the driver's eye being open. In one example, when the vehicle is a car, the image capturing device is placed on a dashboard or near a rearview mirror in the car such that the image capturing device can be directed towards the driver's eyes. For example, the image capturing device includes a camera that can capture hyper-spectral profile of each pixel in a frame. At block 504, spectral profiles from various points in an eye and skin including an eyelid are determined in the captured spectral profiles. In one example, the spectral profiles of the eye include spectral profiles of pupil, iris and/or sclera. The spectral profiles of the eye and the skin including the eyelid are different as the eye have more absorbance capacity due to fluid content present in the eye and the skin has more reflectance capacity.

At block 506, spectral profiles from a sequence of frames substantially around the vehicle driver's eye are captured, in real-time, during a predetermined time interval. For example, the predetermined time interval is about 1 to 2 seconds. In other words, the sequence of frames is captured substantially around the vehicle driver's eye while driving by the image capturing device in the vehicle. In some embodiments, significant deviation in a driver's position (i.e., the driver is not in a designated driving position) is then determined in each of the sequence of frames by correlating each of the sequence of the frames with the frame captured prior to the start of the journey. If there is a significant deviation in the driver's position, then an alarm is generated to the driver. If there is no significant deviation in the driver's position, process steps from block 508 are continued.

At block 508, spectral profiles of the eye and the skin including the eyelid are determined in each of the sequence of frames. In one embodiment, the spectral profiles of the eye and the skin including the eyelid are determined in each of the frames by comparing the spectral profiles of each frame with the spectral profiles obtained at block 504. At block 510, a number of the spectral profiles of the eye and a number of the spectral profiles of the skin including the eyelid in each frame are determined. At block 512, a ratio of the number of the spectral profiles of the eye and the number of the spectral profiles of the skin including the eyelid is determined in each frame. In some embodiments, a state of the driver's eye (e.g., an open state or a closed state or a partially open state) in each frame is then determined based on the associated ratio. In other words, a rate at which the driver's eye is open or closed is determined based on the determined ratio. In one example, the state of the subject's eye in a frame is detected as the open state when the determined ratio is greater than a predetermined threshold. In another example, the state of the subject's eye in a frame is detected as the closed state or the partially open state when the determined ratio is less than the predetermined threshold.

At block 514, a check is made to determine whether the ratio is changing (in the present example, decreasing) over the sequence of frames. If the ratio is changing over the sequence of frames, an alert indicating a drowsiness state of the driver is generated at block 516. For example, the drowsiness state includes gradual drowsiness or persistent drowsiness. In one example, the ratio decreases over the sequence of frames when the driver is falling asleep. In one embodiment, an alert indicating the gradual drowsiness of the driver is generated when the spectral profiles of the skin including the eyelid gradually increases over the sequence of frames (e.g., the driver is falling asleep). In another embodiment, an alert indicating the persistent drowsiness of the driver is generated when there are only spectral profiles of the skin in the sequence of frames (e.g., the driver has closed his eyes in the sequence of frames or the driver is not looking at the road). If the ratio is not changing over the sequence of frames (e.g., the driver is awake or the driver is blinking normally), the process steps from block 506 are continued to detect the driver's wakefulness or drowsiness in next predetermined time intervals.

Figure 6:
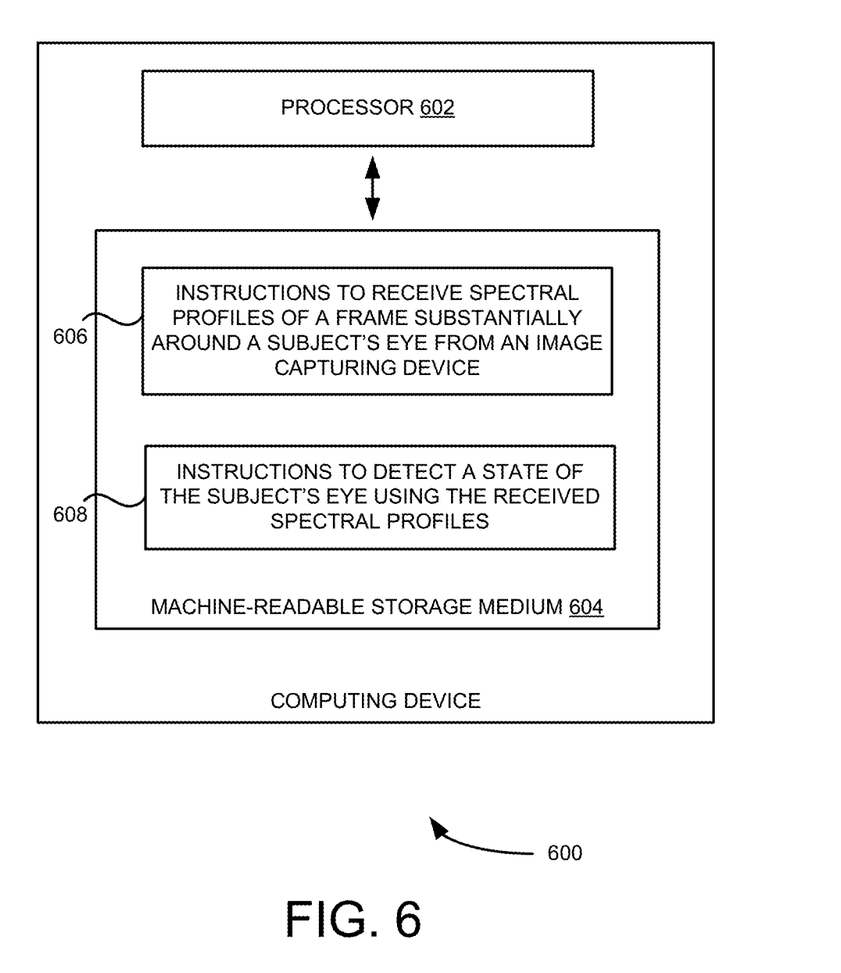
FIG. 6 illustrates a block diagram of a computing device for monitoring subject's eyes, according to one embodiment.

Referring now to FIG. 6, which illustrates a block diagram of an example computing device 600 for monitoring subject's eyes. The computing device 600 includes a processor 602 and a machine-readable storage medium 604 communicatively coupled through a system bus. In an example, the computing device 600 may be analogous to the camera system 102 of FIG. 1. The processor 602 may be any type of a central processing unit (CPU), a microprocessor, or processing logic that interprets and executes machine-readable instructions stored in the machine-readable storage medium 604. The machine-readable storage medium 604 may be a random access memory (RAM) or another type of dynamic storage device that may store information and machine-readable instructions that may be executed by the processor 602. For example, the machine-readable storage medium 604 may be synchronous DRAM (SDRAM), double data rate (DDR), rambus DRAM (RDRAM), rambus RAM, etc. or a storage memory media such as a floppy disk, a hard disk, a CD-ROM, a DVD, a pen drive, and the like. In an example, the machine-readable storage medium 604 may be a non-transitory machine-readable medium. The machine-readable storage medium 604 may store instructions 606 and 608. In an example, the instructions 606 may be executed by the processor 602 to receive spectral profiles of a frame substantially around a subject's eye from an image capturing device. The instructions 608 may be executed by the processor 602 to detect a state of the subject's eye using the received spectral profiles.

In various embodiments, the systems and methods described in FIGS. 1-6 propose a technique for monitoring subject's eyes. The proposed technique determines a rate at which the subject's eyes are open or closed using the spectral profiles of the subject's eyes and the spectral profiles of the skin including eyelids. Thus lowering computing power and time required to detect subject's wakefulness or drowsiness. Also, the proposed technique does not provide false alerts when the subject is blinking his eyes as the subject's drowsiness is detected over a sequence of frames.

Although certain methods, systems, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A camera system comprising:
   an image capturing device configured to capture spectral profiles from a frame substantially around a subject's eye; and
   an eye monitoring system communicatively connected to the image capturing device, wherein the eye monitoring system is configured to:
   receive the spectral profiles of the frame from the image capturing device;
   determine spectral profiles of an eye and skin including an eyelid in the received spectral profiles;
   determine a number of the spectral profiles of the eye and a number of the spectral profiles of the skin including the eyelid;
   determine a ratio of the number of the spectral profiles of the eye and the number of the spectral profiles of the skin including the eyelid; and
   detect a state of the subject's eye in the frame using the determined ratio.

2. The system of claim 1, wherein the eye monitoring system is configured to determine spectral profiles of at least one of a pupil, iris, or sclera in the received spectral profiles.

3. The system of claim 1, wherein the eye monitoring system is configured to:
   obtain spectral profiles of a reference frame substantially around the subject's eye;
   compare the received spectral profiles of the frame with the spectral profiles of the reference frame; and
   determine the spectral profiles of the eye and the skin including the eyelid in the received spectral profiles based on the comparison.

4. The system of claim 1, wherein the eye monitoring system is configured to:
   determine whether the ratio is greater than a predetermined threshold;
   if so, detect the state of the subject's eye in the frame as an open state; and
   if not, detect the state of the subject's eye in the frame as a closed state or a partially open state.

5. The system of claim 1, wherein the eye monitoring system is configured to receive the spectral profiles of the frame from the image capturing device and to detect a state of the subject's eye in the frame using the received spectral profiles, for a number of subsequent frames substantially around the subject's eye to detect a state of the subject's eye in the number of subsequent frames.

6. The system of claim 5, wherein the eye monitoring system is configured to generate an alert based on the state of the subject's eye in the frame and the number of subsequent frames.

7. The system of claim 5, wherein the eye monitoring system is configured to:
   determine whether the ratio of the number of the spectral profiles of the eye and the number of the spectral profiles of the skin including the eyelid is changing over the frame and the number of subsequent frames; and
   detect a drowsiness state of the subject when the ratio is changing over the frame and the number of subsequent frames.

8. The system of claim 7, wherein the eye monitoring system is configured to generate an alert upon detecting the drowsiness state of the subject.

9. The system of claim 7, wherein the eye monitoring system is configured to detect the drowsiness state of the subject when the ratio is decreasing over the frame and the number of subsequent frames.

10. The system of claim 7, wherein the eye monitoring system is configured to:
    detect gradual drowsiness of the subject when the ratio changes gradually over the frame and the number of subsequent frames; and
    detect persistent drowsiness of the subject when the ratio changes significantly over the frame and the number of subsequent frames.

11. A method for monitoring a subject's eye, comprising:
    receiving spectral profiles of a frame substantially around a subject's eye from an image capturing device;
    determining spectral profiles of an eye and skin including an eyelid in the received spectral profiles;
    determining a number of the spectral profiles of the eye and a number of the spectral profiles of the skin including the eyelid;

determining a ratio of the number of the spectral profiles of the eye and the number of the spectral profiles of the skin including the eyelid; and detecting a state of the subject's eye in the frame based on the determined ratio.

12. The method of claim 11, further comprising comparing the received spectral profiles of the frame with spectral profiles of a reference frame substantially around the subject's eye, and wherein determining the spectral profiles of the eye and the skin including the eyelid in the received spectral profiles is based on the comparison.

13. The method of claim 11, further comprising:
receiving spectral profiles of a number of subsequent frames substantially around the subject's eye; and
detecting a state of the subject's eye in the number of subsequent frames.

14. The method of claim 13, further comprising:
determining whether the ratio of the number of the spectral profiles of the eye and the number of the spectral profiles of the skin including the eyelid is changing over the frame and the number of subsequent frames; and
detecting a drowsiness state of the subject when the ratio is changing over the frame and the number of subsequent frames.

15. The method of claim 14, further comprising generating an alert upon detecting the drowsiness state of the subject.

16. A non-transitory computer-readable storage medium comprising instructions for monitoring a subject's eye, the instructions executable by a computing device to:
receive spectral profiles of a frame substantially around a subject's eye from an image capturing device;
determine spectral profiles of an eye and skin including an eyelid in the received spectral profiles;
determine a number of the spectral profiles of the eye and a number of the spectral profiles of the skin including the eyelid;
determine a ratio of the number of the spectral profiles of the eye and the number of the spectral profiles of the skin including the eyelid; and
detect a state of the subject's eye in the frame based on the determined ratio.

17. The non-transitory computer-readable storage medium of claim 16, further comprising instructions executable by a computing device to compare the received spectral profiles of the frame with spectral profiles of a reference frame substantially around the subject's eye, and wherein determining the spectral profiles of the eye and the skin including the eyelid in the received spectral profiles is based on the comparison.

18. The non-transitory computer-readable storage medium of claim 16, further comprising instructions executable by a computing device to:
receive spectral profiles of a number of subsequent frames substantially around the subject's eye; and
detect a state of the subject's eye in the number of subsequent frames.

19. The non-transitory computer-readable storage medium of claim 18, further comprising instructions executable by a computing device to:
determine whether the ratio of the number of the spectral profiles of the eye and the number of the spectral profiles of the skin including the eyelid is changing over the frame and the number of subsequent frames; and
detect a drowsiness state of the subject when the ratio is changing over the frame and the number of subsequent frames.

20. The non-transitory computer-readable storage medium of claim 19, further comprising instructions executable by a computing device to generate an alert upon detecting the drowsiness state of the subject.

* * * * *